US00PP34196P2

(12) United States Plant Patent
Oudshoorn

(10) Patent No.: US PP34,196 P2
(45) Date of Patent: May 3, 2022

(54) ***EUPATORIUM* PLANT NAMED 'DOEUPLIPY'**

(50) Latin Name: *Eupatorium maculatum*
Varietal Denomination: Doeuplipy

(71) Applicant: HERBERT OUDSHOORN B.V., Rijpwetering (NL)

(72) Inventor: Herbert Oudshoorn, Rijpwetering (NL)

(73) Assignee: HERBERT OUDSHOORN B.V., Rijpwetering (NL)

( * ) Notice: Subject to any disclaimer, the term of this patent is extended or adjusted under 35 U.S.C. 154(b) by 0 days.

(21) Appl. No.: 17/499,750

(22) Filed: Oct. 12, 2021

(51) Int. Cl.
*A01H 6/14* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — C. Anne Whealy

(57) ABSTRACT

A new and distinct cultivar of *Eupatorium* plant named 'Doeuplipy', characterized by its relatively compact and broadly upright plant habit; freely branching habit; freely flowering habit; large purple-colored inflorescences; and good container and garden performance.

1 Drawing Sheet

Botanical designation: *Eupatorium maculatum.*
Cultivar denomination: 'DOEUPLIPY'.

STATEMENT REGARDING PRIOR DISCLOSURES BY INVENTOR & APPLICANT/ASSIGNEE

An European Community Plant Breeder's Rights application for the instant plant was filed by the Inventor and Applicant on May 4, 2021, application number 2021/1218. Foreign priority is not claimed to this application.

The Inventor and Applicant assert that no publications nor advertisements relating to sales, offers for sale or public distribution occurred more than one year prior to the effective filing date of this application. Any information about the claimed plant would have been obtained from a direct or indirect disclosure from the Inventor and Applicant. Inventor and Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Eupatorium* plant, botanically known as *Eupatorium maculatum*, commonly referred to as Joe-Pye Weed and hereinafter referred to by the name 'Doeuplipy'.

The new *Eupatorium* plant is a product of a planned breeding program conducted by the Inventor in Rijpwetering, The Netherlands. The objective of the breeding program is to create new compact *Eupatorium* plants that are suitable as container and garden plants.

The new *Eupatorium* plant originated from an open-pollination in August, 2015 in Rijpwetering, The Netherlands of *Eupatorium maculatum* 'Phantom', disclosed in U.S. Plant Pat. No. 18,354, as the female, or seed parent with an unknown selection of *Eupatorium maculatum*, as the male, or pollen, parent. The new *Eupatorium* plant was discovered and selected by the Inventor as a single flowering plant from within the progeny of the stated open-pollination in a controlled outdoor nursery environment in Rijpwetering, The Netherlands in September, 2016.

Asexual reproduction of the new *Eupatorium* plant by terminal vegetative cuttings in a controlled greenhouse environment in Rijpwetering, The Netherlands since September, 2016 has shown that the unique features of this new *Eupatorium* plant are stable and reproduced true to type in successive generations.

SUMMARY OF THE INVENTION

Plants of the new *Eupatorium* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Doeuplipy'. These characteristics in combination distinguish 'Doeuplipy' as a new and distinct *Eupatorium* plant:

1. Relatively compact and broadly upright plant habit.
2. Freely branching habit.
3. Freely flowering habit.
4. Large purple-colored inflorescences.
5. Good container and garden performance.

Plants of the new *Eupatorium* differ primarily from plants of the female parent, 'Phantom', in plant habit as plants of the new *Eupatorium* are more compact than and not as tall as plants of 'Phantom'.

Plants of the new *Eupatorium* can be compared to plants of *Eupatorium maculatum* 'Snowball', disclosed in U.S. Plant Pat. No. 22,869. In side-by-side comparisons, plants of the new *Eupatorium* differ primarily from plants of 'Snowball' in plant habit as plants of the new *Eupatorium* are more compact than and not as tall as plants of 'Snowball'. In addition, plants of the new *Eupatorium* have purple-colored inflorescences whereas plants of 'Snowball' have creamy white-colored inflorescences.

BRIEF DESCRIPTION OF THE PHOTOGRAPH

The accompanying photograph illustrates the overall appearance of the new *Eupatorium* plant showing the colors as true as it is reasonably possible to obtain in colored reproductions of this type. Colors in the photographs may differ slightly from the color values cited in the detailed botanical description which accurately describe the colors of the new *Eupatorium* plant. The photograph is a side perspective view of a typical flowering plant of 'Doeuplipy' grown in a container.

DETAILED BOTANICAL DESCRIPTION

The aforementioned photograph and following observations and measurements describe plants grown during the summer in 17-cm containers in an outdoor nursery in Aalsmeer, The Netherlands and under cultural practices typical of commercial *Eupatorium* production. During the production of the plants, average daily temperatures were 22° C. and average night temperatures were 17° C. Plants were three months old when the photograph was taken and 16 weeks old when the description was taken. In the following description, color references are made to The Royal Horticultural Society Colour Chart, Second Edition, except where general terms of ordinary dictionary significance are used.

Botanical classification: *Eupatorium maculatum* 'Doeuplipy'.

Parentage:

*Female parent.*—*Eupatorium maculatum* 'Phantom', disclosed in U.S. Plant Pat. No. 18,354.

*Male parent.*—Unknown selection of *Eupatorium maculatum*, not patented.

Propagation:

*Type.*—Terminal vegetative cuttings.

*Time to initiate roots, summer.*—About twelve days at temperatures about 26° C.

*Time to initiate roots, winter.*—About 14 days at temperatures about 23° C.

*Time to produce a rooted cutting, summer.*—About 14 days at temperatures about 23° C.

*Time to produce a rooted cutting, winter.*—About 16 days at temperatures about 18° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching habit; medium density.

Plant description:

*Plant and growth habit.*—Perennial plant appropriate as a container or garden plant; relatively compact and broadly upright plant habit; not vigorous, yet moderate growth rate; freely basal branching habit with about 20 primary branches developing per plant.

*Plant height.*—About 80 cm.

*Plant diameter or spread.*—About 50 cm.

*Lateral branches.*—Length: About 65 cm. Diameter: About 1 cm. Internode length: About 11 cm. Aspect: Upright to about 25° from vertical. Strength: Strong. Texture and luster: Smooth, glabrous; glossy. Color, developing: Close to 144B. Color, developed: Close to 187A with 144A.

Leaf description:

*Arrangement.*—Opposite, simple.

*Length.*—About 13 cm.

*Width.*—About 6 cm.

*Shape.*—Narrowly ovate to lanceolate.

*Apex.*—Acute.

*Base.*—Cuneate.

*Margin.*—Senate.

*Texture and luster, upper surface.*—Smooth, glabrous; semi-glossy.

*Texture and luster, lower surface.*—Smooth, glabrous; matte.

*Venation pattern.*—Pinnate, reticulate.

*Color.*—Developing leaves, upper surface: Close to 139A. Developing leaves, lower surface: Close to 147B. Fully expanded leaves, upper surface: Close to 147A; venation, close to 147A. Fully expanded leaves, lower surface: Close to 146A; venation, close to 145A.

*Petioles.*—Length: About 2.2 cm. Diameter: About 3 mm. Color, upper surface: Close to 187A. Color, lower surface: Close to 144B. Texture and luster, upper and lower surfaces: Smooth, glabrous; glossy.

Inflorescence description:

*Arrangement and habit.*—Discoid inflorescences arranged in terminal and axillary compound corymbs; inflorescences face mostly upright; freely flowering habit, with about 230 inflorescences per terminal corymb with numerous corymbs developing per plant; ray floret development has not been observed on plants of the new *Eupatorium.*

*Fragrance.*—Faintly fragrant; sweet.

*Time to flower.*—Plants flower continuously from July to September in The Netherlands.

*Inflorescence buds.*—Height: About 9 mm. Diameter: About 3 mm. Shape: Elliptic. Texture and luster: Smooth, glabrous; glossy. Color: Close to 84A.

*Corymb diameter.*—About 15 cm.

*Corymb height.*—About 14 cm.

*Inflorescence diameter.*—About 8 mm.

*Inflorescence height.*—About 1 cm.

*Disc diameter.*—About 2 mm.

*Receptacle diameter.*—About 1 mm.

*Receptacle height.*—Less than 1 mm.

*Receptacle shape.*—Rounded; button-shape.

*Receptacle color.*—Close to 143A.

*Disc florets.*—Quantity and arrangement: About twelve arranged in about two whorls at the center of the receptacle. Length: About 1 cm. Diameter: About 1 mm. Shape: Tubular, fused towards the base. Apex: Acute. Margin: Entire. Texture and luster, upper and lower surfaces: Smooth, glabrous; glossy. Color, when opening and fully opened, upper and lower surfaces: Close to 84A; venation, close to 84A; with subsequent development, color becoming closer to 73A.

*Phyllaries.*—Quantity and arrangement: About 21 arranged in about four whorls; imbricate. Length: About 5 mm. Width: About 2 mm. Shape: Elliptic. Apex: Obtuse. Base: Cuneate. Margin: Entire, ciliate. Texture and luster, upper and lower surfaces:

Smooth, glabrous; glossy. Color, upper surface: Close to 84A and 143B. Color, lower surface: Close to 84D and 143B.

*Peduncles*.—Length, terminal peduncle: About 5 mm. Diameter, terminal peduncle: About 1 mm. Length, third peduncle: About 3 cm. Diameter, terminal peduncle: About 1 mm. Strength: Flexible. Aspect: About 40° from lateral branch axis. Texture and luster: Smooth, glabrous; matte. Color: Close to 177A.

*Pedicels*.—Length: About 3 mm. Diameter: About 1 mm. Strength: Flexible. Aspect: Upright to about 30° from peduncle axis. Texture and luster: Smooth, glabrous; matte. Color: Close to 177B.

*Reproductive organs*.—Androecium: Quantity per disc floret: About five. Filament length: About 1 mm. Filament color: Close to 84A. Anther shape: Oblong; basifixed Anther size: About 0.1 mm by 2 mm. Anther color: Close to 200B. Pollen amount: Moderate. Pollen color: Close to 8C. Gynoecium: Quantity per disc floret: One. Pistil length: About 8 mm. Stigma diameter: About 1 mm. Stigma shape: Bifid. Stigma color: Close to 84A. Style length: About 5 mm. Style color: Close to 84A. Ovary color: Close to 145A. Seeds and fruits: To date, seed and fruit development have not been observed on plants of the new *Eupatorium*.

Pathogen & pest resistance: To date, plants of the new *Eupatorium* have not been shown to be resistant to pathogens and pests common to *Eupatorium*.

Garden performance: Plants of the new *Eupatorium* have exhibited good garden performance and to tolerate rain, wind, temperatures ranging from about −30° C. to about 30° C. and to be suitable for U.S.D.A. Hardiness Zone 4.

It is claimed:

1. A new and distinct *Eupatorium* plant named 'Doeuplipy' as illustrated and described.

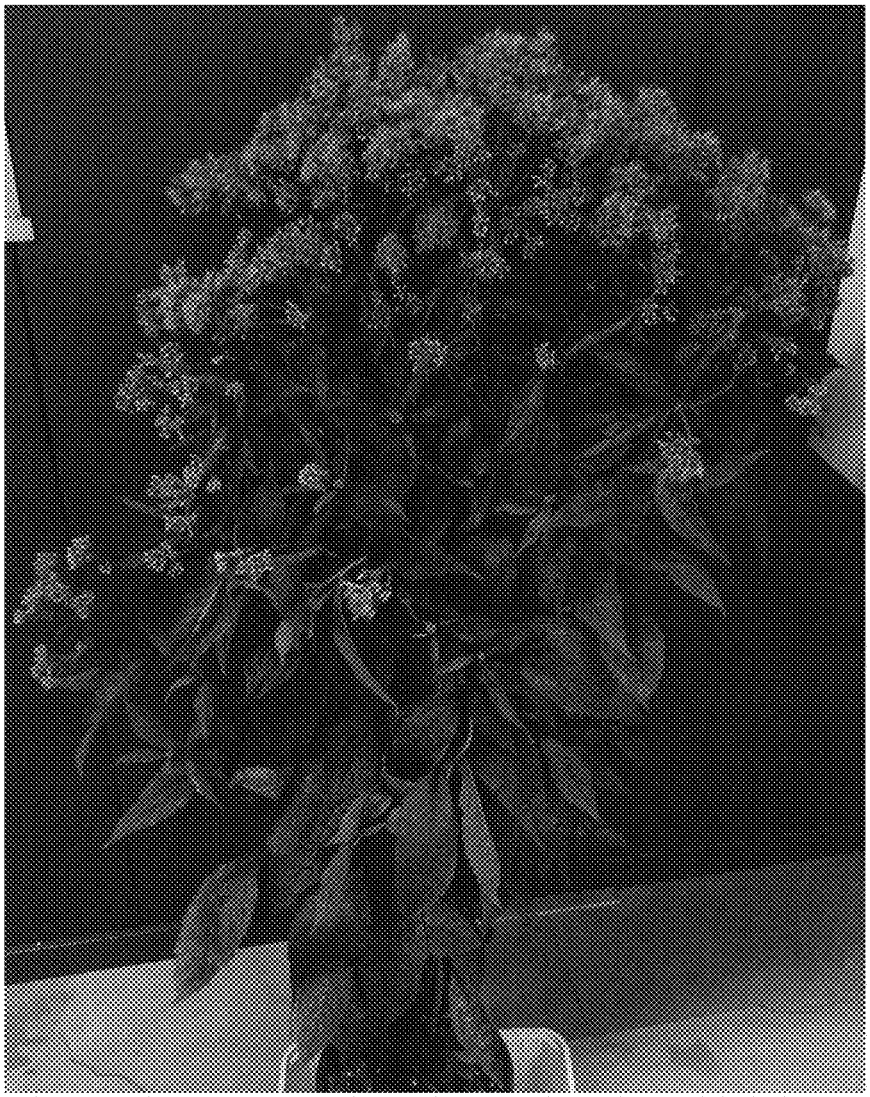

* * * * *